United States Patent [19]
Hurle et al.

[11] Patent Number: 5,916,758
[45] Date of Patent: Jun. 29, 1999

[54] SMOOTH MUSCLE CELL-DERIVED MIGRATION FACTOR

[76] Inventors: Mark Robert Hurle; Peter Colon McDonnell; Dean Edward McNulty, all of SmithKline Beecham Corporation Corporate Intellectual Property-U.S., UW2220 P.O. Box 1539, King of Prussia, Pa. 19406-0939; Craig Alan Rosen, Human Genome Sciences, Inc. 9410 Key West Ave., Rockville, Md. 20850-3338; Ivo Rogulja Siemens, SmithKline Beecham Corporation Corporate Intellectual Property-U.S., UW2220 P.O. Box 1539, King of Prussia, Pa. 19406-0939; Peter Ronald Young, SmithKline Beecham Corporation Corporate Intellectual Property-U.S., UW2220 P.O. Box 1539, King of Prussia, Pa. 19406-0939; Tian-Li Yue, SmithKline Beecham Corporation Corporate Intellectual Property-U.S., UW2220 P.O. Box 1539, King of Prussia, Pa. 19406-0939

[21] Appl. No.: 08/839,008

[22] Filed: Apr. 23, 1997

Related U.S. Application Data

[62] Division of application No. 08/563,697, Nov. 28, 1995, abandoned
[60] Provisional application No. 60/003,344, Sep. 8, 1995.

[51] Int. Cl.$^6$ .................................................. G01N 33/53
[52] U.S. Cl. ........................... 435/7.8; 435/7.1; 435/325; 530/350; 436/501
[58] Field of Search ............................ 435/7.1, 7.8, 325; 436/501; 530/350

[56] References Cited

FOREIGN PATENT DOCUMENTS 06107694 of 1994 Japan .

OTHER PUBLICATIONS

F. Ayala and J. Kiger, *Modern Genetics*. Benjamin/Cummings Publishing Co., Inc., p. 45 (1990).

Morisaki, et al., "Purification and Characterization of an Autocrine Migration Factor for Vascular Smooth Muscle Cells, SMC–Derived Migration Factor, and Its Role in Arteriosclerosis", *Annals New York Academy of Sciences*, pp. 575–577 (Jan. 17, 1995).

Lecain, et al., "Isolation of a Novel cDNA Corresponding to a Transcript Expressed in the Choroid Plexus and Leptomeninges", *Journal of Neurochemistry*, 56 No. 6, 2133–2138 (1991).

Koyama, et al., "Purification and Characterization of an Autocrine Migration Factor for Vascular Smooth Muscle Cells (SMC), SMC–derived Migration Factor", *The Journal of Biological Chemistry*, 268 No. 18, pp. 13301–13308 (1993).

Koyama, et al., "Secretion of a potent new migration factor for smooth muscle cells (SMC) by cultured SMC", *Atherosclerosis*, 86, pp. 219–226 (1991).

Takahara, et al., "Type I Procollagen COOH–terminal Proteinase Enhancer Protein: Identification, Primary Structure, and Chromosomal Localization of the Cognate Human Gene (PCOLCE)", *The Journal of Biological Chemistry*, 269 No. 42, pp. 26280–26285 (1994).

Morisaki et al., *J. Jpn. Atheroscler. Soc.*, pp. 615–630, 18/6 (1990).

Koyama et al., "Autocrine Migration Mechanism in Smooth Muscle Cells by Smooth Muscle Cell–Derived Migration Factor and Relationship to Atheroma Formation", *Japanese Circulation Journal*, 53 pp. 897–898 (1989).

Koyama et al., "Inhibitory Effect of Ginsenosides on Migration of Arterial Smooth Muscle Cells", *American Journal of Chinese Medicine*, 20 No. 2, pp. 167–173 (192).

Moisaki, et al., "Purification and Characterization of an Autocrine Migration Factor for Vascular Smooth Muscle cells (SMC), SMC–derived Migration Factor (SDMF)", *66th Scientific Sessions of the American Heart Association, Circ. 88 (4 part 2)*, p. 1240 (1993).

*Primary Examiner*—Lila Feisee
*Assistant Examiner*—Eliane Lazar-Wesley
*Attorney, Agent, or Firm*—Kirk Baumeister; Charles M. Kinzig

[57] ABSTRACT

Isolated nucleic acid encoding human smooth muscle cell-derived migration factor, protein obtainable from the nucleic acid, recombinant host cells transformed with the nucleic acid and use of the protein and nucleic acid sequence are disclosed.

1 Claim, 3 Drawing Sheets

```
  1 MLPAATASLLGPLLTACALLPFAQGQTPNYTRPVFLCGGDVKGESGYVAS  50
    *****  *:***:*  *   :**:* ********************* *******
  1 MLPAALTSFLGPFLLA.WVLPLARGQTPNYTRPVFLCGGDVTGESGYVAS  49

51 EGFPNLYPPNKECIWTITVPEGQTVSLSFRVFDLELHPACRYDALEVFAG 100
    **********.*********************:**** .**********
 50 EGFPNLYPPNKKCIWTITVPEGQTVSLSFRVFDMELHPSCRYDALEVFAG  99

101 SGTSGQRLGRFCGTFRPAPLVAPGNQVTLRMTTDEGTGGRGFLLWYSGRA 150
    *****************:*******************************
100 SGTSGQRLGRFCGTFRPAPVVAPGNQVTLRMTTDEGTGGRGFLLWYSGRA 149

151 TSGTEHQFCGGRLEKAQGTLTTPNWPESDYPPGISCSWHIIAPPDQVIAL 200
    ***********:*************** *************.:*** *
150 TSGTEHQFCGGRMEKAQGTLTTPNWPESYYPPGISCSWHIIAPSNQVIML 199

201 TFEKFDLEPDTYCRYDSVSVFNGAVSDDSRRLGKFCGDAVPGSISSEGNE 250
    **:***:*********************:******** .*:.*******
200 TFGKFDVEPDTYCRYDSVSVFNGAVSDDSKRLGKFCGDKAPSPISSEGNE 249

251 LLVQFVSDLSVTADGFSASYKTLPRGTAKEGQG..............PGP 286
    ********************:****:.....: :            .:*
250 LLVQFVSDLSVTADGFSASYRTLPRDAVEKESALSPGEDVQRGPQSRSDP 299

287 KRGTEPKVKLP..PKSQPPEKTEESPS......APDAP..TCPKQCRRTG 326
    * **:****  * *****:*..*.**.      **.**  *****::*.*
300 KTGTGPKVKPPTKPKSQPAETPEASPATQATPVAPAAPSITCPKQYKRSG 349

327 TLQSNFCASSLVVTATVKSMVREPGEGLAVTVSLIGAYKTGGLDLPSPPT 376
    *******.******:*** *** ****** *****:*.************.
350 TLQSNFCSSSLVVTGTVKTMVRGPGEGLTVTVSLLGVYKTGGLDLPSPPS 399

377 GASLKFYVPCKQCPPMKKGVSYLLMGQVEENRGPVLPPESFVVLHRPNQD 426
    *.***:****:* ******.************:*********.*.***
400 GTSLKLYVPCRQMPPMKKGASYLLMGQVEENRGPILPPESFVVLYRSNQD 449

427 QILTNLSKRKCPSQPVRAA 445
    ***.********* **
450 QILNNLSKRKCPSQPRTAA 468
```

FIG. 1

```
  1 MLPAATASLLGPLLTACALLPFAQGQTPNYTRPVFLCGGDVKGESGYVAS  50
    **************************************************
  1 MLPAATASLLGPLLTACALLPFAQGQTPNYTRPVFLCGGDVKGESGYVAS  50

51 EGFPNLYPPNKECIWTITVPEGQTVSLSFRVFDLELHPACRYDALEVFAG 100
    ****  ********************************************
 51 EGFPNSYPPNKECIWTITVPEGQTVSLSFRVFDLELHPACRYDALEVFAG 100

101 SGTSGQRLGRFCGTFRPAPLVAPGNQVTLRMTTDEGTGGRGFLLWYSGRA 150
    **************************************************
101 SGTSGQRLGRFCGTFRPAPLVAPGNQVTLRMTTDEGTGGRGFLLWYSGRA 150

151 TSGTEHQFCGGRLEKAQGTLTTPNWPESDYPPGISCSWHIIAPPDQVIAL 200
    *** .*********************************************
151 TSGSEHQFCGGRLEKAQGTLTTPNWPESDYPPGISCSWHIIAPPDQVIAL 200

201 TFEKFDLEPDTYCRYDSVSVFNGAVSDDSRRLGKFCGDAVPGSISSEGNE 250
    **************************************************
201 TFEKFDLEPDTYCRYDSVSVFNGAVSDDSRRLGKFCGDAVPGSISSEGNE 250

251 LLVQFVSDLSVTADGFSASYKTLPRGTAKEGQGPGPKRGTEPKVKLPPKS 300
    **************************************************
251 LLVQFVSDLSVTADGFSASYKTLPRGTAKEGQGPGPKRGTEPKVKLPPKS 300

301 QPPEKTEESPSAPDAPTCPKQCRRTGTLQSNFCASSLVVTATVKSMVREP 350
    **************************************************
301 QPPEKTEESPSAPDAPTCPKQCRRTGTLQSNFCASSLVVTATVKSMVREP 350

351 GEGLAVTVSLIGAYKTGGLDLPSPPTGASLKFYVPCKQCPPMKKGVSYLL 400
    ********************** .**************************
351 GEGLAVTVSLIGAYKTGGLDLPTPPTGASLKFYVPCKQCPPMKKGVSYLL 400

401 MGQVEENRGPVLPPESFVVLHRPNQDQILTNLSKRKCPSQPVRAAASQD  449
    **************************************************
401 MGQVEENRGPVLPPESFVVLHRPNQDQILTNLSKRKCPSQPVRAAASQD  449
```

SMOOTH MUSCLE CELL-DERIVED MIGRATION FACTOR

This is a divisional of application Ser. No. 08/563,697, filed Nov. 28, 1995, now abandoned which claims the benefit of U.S. Provisional Application No. 60/003,344, filed Sep. 8, 1995.

FIELD OF THE INVENTION

The present invention relates to an isolated human smooth muscle cell-derived migration factor (SDMF) gene; to essentially pure human SDMF protein; and to compositions and methods of producing and using human SDMF sequences and proteins.

BACKGROUND OF THE INVENTION

Migration of arterial smooth muscle cells (SMC) into the intimal layer of blood vessel walls is a key event in the development of atherosclerotic lesions and also of restenosis after coronary balloon angioplasty. A number of SMC migration factors secreted by vascular cells or derived from other blood components have been identified. These migration factors include platelet-derived growth factor, interleukin-1, transforming growth factor-β, fibronectin, vitronectin, fibrinogen and oxidized low density lipoprotein.

Smooth muscle cell-derived migration factors (SDMF) from rat and rabbit have been described by Koyama et al. in *Atherosclerosis* 86, 219–226 (1991). Subsequent purification and biochemical and pharamacological studies of the rat SDMF protein from aortic SMC were reported by the same group in Koyama et al., *J. Biol. Chem.* 268, 13301–13308 (1993).

The studies indicated that rat SDMF is a potent SMC migration factor which does not enhance proliferation of SMC. The 58 kDa SMC-secreted protein differed biochemically from other know SMC migration factors and was reported to induce migration by an autocrine mechanism. Sequencing and/or cloning of the rat SDMF was not reported.

SMC migration is involved in a number of blood vessel pathologies. As a SMC autocrine migratory factor, SDMF is thought to play an important role in blood vessel pathology, e.g., the formation of intimal thickening of atherosclerotic lesions. The involvement of SDMF in the regulation of SMC migration necessitates the full identification of SDMF and its cDNA. A need also exists for compounds which modulate the activity of SDMF, for methods to identify such modulators and for reagents useful in such methods.

SUMMARY OF THE INVENTION

Accordingly, one aspect of the present invention is an isolated polynucleotide selected from the group consisting of:
(a) a polynucleotide encoding human SDMF having the nucleotide sequence as set forth in SEQ ID NO:1 from nucleotide 94 to 1440;
(b) a polynucleotide capable of hybridizing to the complement of a polynucleotide according to (a) under moderately stringent hybridization conditions and which encodes a functional human SDMF; and
(c) a degenerate polynucleotide according to (a) or (b).

Another aspect of the invention is a functional polypeptide encoded by the polynucleotides of the invention.

Another aspect of the invention is a method for preparing essentially pure human SDMF protein comprising culturing a recombinant host cell comprising a vector comprising a polynucleotide of the invention under conditions promoting expression of the protein and recovery thereof.

Another aspect of the invention is an antisense oligonucleotide comprising a sequence which is capable of binding to the polynucleotide of the invention.

Another aspect of the invention is a modulator of the polypeptides of the invention.

Another aspect of the invention is a method for assaying a medium for the presence of a substance that modulates SDMF activity comprising the steps of:
(a) providing a SDMF protein having the amino acid sequence of SDMF (SEQ ID NO:2) or a functional derivative thereof and SMC in a chamber;
(b) adding a test substance which is suspected of modulating SDMF activity to either the SDMF or SMC;
(c) incubating the chamber under conditions which permit the migration of SMC;
(d) counting the number of migrated and nonmigrated SMC; and
(e) comparing to a control to determine the effect of the test substance.

Another aspect of the invention is a method for assaying a medium for the presence of a substance that modulates SDMF activity comprising the steps of:
(a) providing a SDMF protein having the amino acid sequence of SDMF (SEQ ID NO:2) or a functional derivative thereof and a cellular binding partner;
(b) incubating with a test substance which is suspected of modulating SDMF activity under conditions which permit the formation of a SDMF protein/cellular binding partner complex;
(c) assaying for the presence of the complex, free SDMF protein or free cellular binding partner; and
(d) comparing to a control to determine the effect of the substance.

Another aspect of the invention is SDMF protein modulating compounds identified by the methods of the invention.

Another aspect of the invention is a method for the treatment of a patient having need to modulate SDMF activity comprising administering to the patient a therapeutically effective amount of the modulating compounds of the invention.

Another aspect of the invention is a method for the treatment of a patient having need of SDMF comprising administering to the patient a therapeutically effective amount of the polypeptide of the invention.

Another aspect of the invention is a pharmaceutical composition comprising a polypeptide of the invention and a pharmaceutically acceptable carrier.

Another aspect of the invention is a method of diagnosing conditions associated with SDMF protein deficiency which comprises:
(a) isolating a polynucleotide sample from an individual;
(b) assaying the polynucleotide sample and a polynucleotide encoding SDMF having the nucleotide sequence as set forth in SEQ ID NO:1 from nucleotide 94 to 1440; and
(c) comparing differences between the polynucleotide sample and the SDMF polynucleotide, wherein any differences indicate mutations in the SDMF gene.

Another aspect of the invention is a method of treating conditions which are related to insufficient SDMF protein function which comprises administering the polynucleotide of claim 1 to a patient deficient in SDMF protein function wherein a SDMF protein is expressed and alleviates the condition.

Yet another aspect of the invention is a transgenic non-human animal capable of expressing in any cell thereof the polynucleotide of the invention.

BRIEF DESCRIPTION OF THE DRAWINGS

FIG. 1 is an amino acid sequence alignment of human SDMF protein with murine p14 protein.

FIG. 2 is an amino acid sequence alignment of human SDMF protein with human PCOLCE protein.

DETAILED DESCRIPTION OF THE INVENTION

Figure 3:
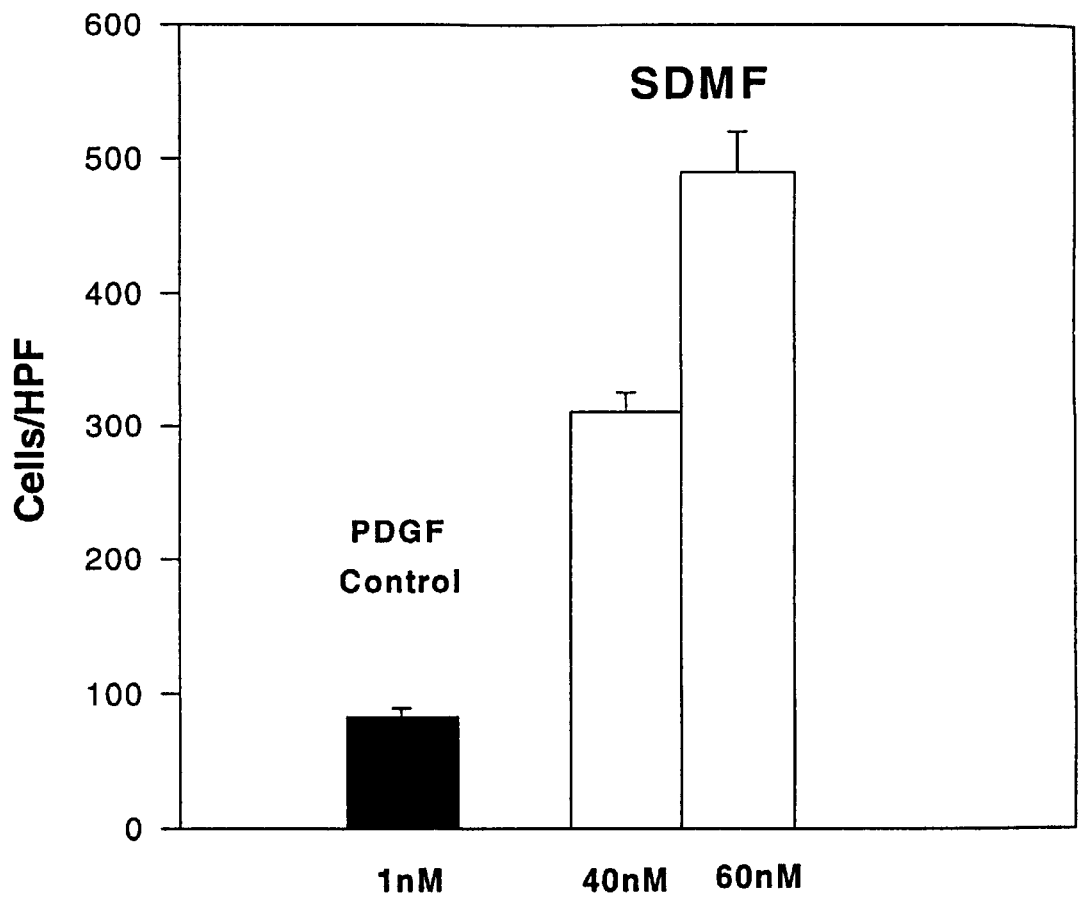
FIG. 3 is a graph of experimental results demonstrating the biological activity of purified human SDMF.

As used herein, the term "SDMF gene" refers to DNA molecules comprising a nucleotide sequence that encodes smooth muscle cell-derived migration factor. The human SDMF gene sequence is listed in SEQ ID NO:1. The coding region of the SDMF gene consists of nucleotides 94–1440 of SEQ ID NO:1. The deduced 449 amino acid sequence of the SDMF gene product is listed in SEQ ID NO:2.

As used herein, the term "functional fragments" when used to modify a specific gene or gene product means a less than full length portion of the gene or gene product which retains substantially all of the biological function associated with the full length gene or gene product to which it relates. To determine whether a fragment of a particular gene or gene product is a functional fragment, fragments are generated by well-known nucleolytic or proteolytic techniques and the fragments tested for the described biological function.

As used herein, an "antigen" refers to a molecule containing one or more epitopes that will stimulate a host's immune system to make a humoral and/or cellular antigen-specific response. The term is also used herein interchangeably with "immunogen."

As used herein, the term "epitope" refers to the site on an antigen or hapten to which a specific antibody molecule binds. The term is also used herein interchangeably with "antigenic determinant" or "antigenic determinant site."

As used herein, "monoclonal antibody" is understood to include antibodies derived from one species (e.g., murine, rabbit, goat, rat, human, etc.) as well as antibodies derived from two, or perhaps more, species (e.g., chimeric and humanized antibodies).

As used herein, a coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

As used herein, "recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

As used herein, a "replicon" is any genetic element (e.g., plasmid, chromosome, virus) that functions as an autonomous unit of DNA replication in vivo; i.e., capable of replication under its own control.

As used herein, a "vector" is a replicon, such as a plasmid, phage, or cosmid, to which another DNA segment may be attached so as to bring about the replication of the attached segment.

As used herein, a "reference" gene refers to the human SDMF gene sequence of the invention and is understood to include the various sequence polymorphisms that exist, wherein nucleotide substitutions in the gene sequence exist, but do not affect the essential function of the gene product.

As used herein, a "mutant" gene refers to human SDMF sequences different from the reference gene wherein nucleotide substitutions and/or deletions and/or insertions result in impairment of the essential function of the gene product.

As used herein, a DNA "coding sequence of" or a "nucleotide sequence encoding" a particular protein, is a DNA sequence which is transcribed and translated into a polypeptide when placed under the control of appropriate regulatory sequences.

As used herein, a "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

As used herein, DNA "control sequences" refers collectively to promoter sequences, ribosome binding sites, polyadenylation signals, transcription termination sequences, upstream regulatory domains, enhancers and the like, which collectively provide for the expression (i.e., the transcription and translation) of a coding sequence in a host cell.

As used herein, a control sequence "directs the expression" of a coding sequence in a cell when RNA polymerase will bind the promoter sequence and transcribe the coding sequence into mRNA, which is then translated into the polypeptide encoded by the coding sequence.

As used herein, a "host cell" is a cell which has been transformed or transfected, or is capable of transformation or transfection by an exogenous DNA sequence.

As used herein, a cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

As used herein, "transfection" or "transfected" refers to a process by which cells take up foreign DNA and integrate that foreign DNA into their chromosome. Transfection can be accomplished, for example, by various techniques in which cells take up DNA (e.g., calcium phosphate precipitation, electroporation, assimilation of liposomes, etc.) or by infection, in which viruses are used to transfer DNA into cells.

As used herein, a "target cell" is a cell(s) that is selectively transfected over other cell types (or cell lines).

As used herein, a "clone" is a population of cells derived from a single cell or common ancestor by mitosis. A "cell line" is a clone of a primary cell that is capable of stable growth in vitro for many generations.

As used herein, a "heterologous" region of a DNA construct is an identifiable segment of DNA within or attached to another DNA molecule that is not found in association with the other molecule in nature. Thus, when the heterologous region encodes a gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

As used herein, a "modulator" of a polypeptide is a substance which can affect the polypeptide function.

An aspect of the present invention is isolated polynucleotides encoding a human SDMF protein and substantially similar sequences. Isolated polynucleotide sequences are substantially similar if they are capable of hybridizing under moderately stringent conditions to SEQ ID NO:1 or they encode DNA sequences which are degenerate to SEQ ID NO:1 or are degenerate to those sequences capable of hybridizing under moderately stringent conditions to SEQ ID NO:1.

Moderately stringent conditions is a term understood by the skilled artisan and has been described in, for example, Sambrook et al. *Molecular Cloning: A Laboratory Manual*, 2nd edition, Vol. 1, pp. 101–104, Cold Spring Harbor Laboratory Press (1989). An exemplary hybridization protocol using moderately stringent conditions is as follows. Nitrocellulose filters are prehybridized at 65° C. in a solution containing 6X SSPE, 5X Denhardt's solution (10 g Ficoll, 10 g BSA and 10 g polyvinylpyrrolidone per liter solution), 0.05% SDS and 100 ug/ml tRNA. Hybridization probes are labeled, preferably radiolabelled (e.g., using the Bios TAG-IT® kit). Hybridization is then carried out for approximately 18 hours at 65° C. The filters are then washed twice in a solution of 2X SSC and 0.5% SDS at room temperature for 15 minutes. Subsequently, the filters are washed at 58° C., air-dried and exposed to X-ray film overnight at −70° C. with an intensifying screen.

Degenerate DNA sequences encode the same amino acid sequence as SEQ ID NO:2 or the proteins encoded by that sequence capable of hybridizing under moderately stringent conditions to SEQ ID NO:1, but have variation(s) in the nucleotide coding sequences because of the degeneracy of the genetic code. For example, the degenerate codons UUU and UUC both code for the amino acid phenylalanine, whereas the four codons GGX all code for glycine.

Alternatively, substantially similar sequences are defined as those sequences in which about 66%, preferably about 75% and most preferably about 90%, of the nucleotides or amino acids match over a defined length of the molecule. As used herein, substantially similar refers to the sequences having similar identity to the sequences of the instant invention. Thus, nucleotide sequences that are substantially the same can be identified by hybridization or by sequence comparison. Protein sequences that are substantially the same can be identified by techniques such as proteolytic digestion, gel electrophoresis and/or microsequencing. Excluded from the definition of substantially similar sequences is the murine p14 sequence reported by Lecain et al. in *J. Neurochem.* 56, 2133–2138 (1991) and the human procollagen C-proteinase enhancer precursor sequence (PCOLCE) reported by Takahara et al. in *J. Biol. Chem.* 269, 26280–26285 (1994).

Embodiments of the isolated polynucleotides of the invention include DNA, genomic DNA and RNA, preferably of human origin. A method for isolating a nucleic acid molecule encoding a SDMF protein is to probe a genomic or cDNA library with a natural or artificially designed probe using art recognized procedures. See, e.g., "Current Protocols in Molecular Biology", Ausubel et al. (eds.) Greene Publishing Association and John Wiley Interscience, New York, 1989,1992. The ordinarily skilled artisan will appreciate that SEQ ID NO:1 or fragments thereof comprising at least 15 contiguous nucleotides are particularly useful probes. It is also appreciated that such probes can be and are preferably labeled with an analytically detectable reagent to facilitate identification of the probe. Useful reagents include, but are not limited to, radioisotopes, fluorescent dyes or enzymes capable of catalyzing the formation of a detectable product. The probes would enable the ordinarily skilled artisan are to isolate complementary copies of genomic DNA, cDNA or RNA polynucleotides encoding SDMF proteins from human, mammalian or other animal sources or to screen such sources for related sequences, e.g., additional members of the family, type and/or subtype, including transcriptional regulatory and control elements as well as other stability, processing, translation and tissue specificity-determining regions from 5' and/or 3' regions relative to the coding sequences disclosed herein, all without undue experimentation.

Another aspect of the invention is functional polypeptides encoded by the polynucleotides of the invention. An embodiment of a functional polypeptide of the invention is the human SDMF protein having the amino acid sequence set forth in SEQ ID NO: 2.

Another aspect of the invention is a method for preparing essentially pure human SDMF protein. Yet another aspect is the human SDMF protein produced by the preparation method of the invention. This protein has the amino acid sequences listed in SEQ ID NO: 2 and include variants with a substantially similar amino acid sequence that have the same function. The proteins of this invention are preferably made by recombinant genetic engineering techniques by culturing a recombinant host cell containing a vector encoding the polynucleotides of the invention under conditions promoting the expression of the protein and recovery thereof.

The isolated polynucleotides, particularly the DNAs, can be introduced into expression vectors by operatively linking the DNA to the necessary expression control regions, e.g., regulatory regions, required for gene expression. The vectors can be introduced into an appropriate host cell such as a prokaryotic, e.g., bacterial, or eukaryotic, e.g., yeast or mammalian cell by methods well known in the art. See Ausubel et al., supra. The coding sequences for the desired proteins, having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include, but are not limited to, the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomzyces), a baculovirus insect cell system, a Drosophila insect system, YCp19 (Saccharomyces) and pSV2neo (mammalian cells). See generally, "DNA Cloning": Vols. I & II, Glover et al. ed. IRL Press Oxford (1985) (1987); and T. Maniatis et al. ("Molecular Cloning" Cold Spring Harbor Laboratory (1982).

The gene can be placed under the control of control elements such as a promoter, ribosome binding site (for bacterial expression) and, optionally, an operator, so that the DNA sequence encoding the desired protein is transcribed into RNA in the host cell transformed by a vector containing the expression construct. The coding sequence may or may not contain a signal peptide or leader sequence. The proteins of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437 and 4,338,397.

In addition to control sequences, it may be desirable to add regulatory sequences which allow for regulation of the expression of the protein sequences relative to the growth of the host cell. Regulatory sequences are known to those of skill in the art. Exemplary are those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences, i.e., RNA polymerase which binds to the DNA molecule at the control sequences transcribes the coding sequence. Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to produce mutants or analogs of human SDMF protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; "DNA Cloning," Vols. I and II, supra; and "Nucleic Acid Hybridization", supra.

Depending on the expression system and host selected, the proteins of the present invention are produced by growing host cells transformed by an expression vector described above under conditions whereby the protein of interest is expressed. Preferred mammalian cells include human embryonic kidney cells (293), monkey kidney cells, fibroblast (COS) cells, Chinese hamster ovary (CHO) cells, Drosophila or murine L-cells. If the expression system secretes the protein into the growth media, the protein can be purified directly from the media. If the protein is not secreted, it is isolated from cell lysates or recovered from the cell membrane fraction. The selection of the appropriate growth conditions and recovery methods are within the skill of the art.

Another aspect of this invention is the operative linking of the polynucleotides of the invention to regulatory elements which are differentially responsive to various temperature or metabolic conditions, thereby effectively turning on or off the phenotypic expression in response to those conditions.

An alternative method to identify proteins of the present invention is by constructing gene libraries, using the resulting clones to transform *E. coli* and pooling and screening individual colonies using polyclonal serum or monoclonal antibodies to human SDMF.

The proteins of the present invention may also be produced by chemical synthesis such as solid phase peptide synthesis on an automated peptide synthesizer, using known amino acid sequences or amino acid sequences derived from the DNA sequence of the genes of interest. Such methods are known to those skilled in the art.

Another aspect of the present invention is modulators of the polypeptides of the invention. Functional modulation of SDMF by a substance includes partial to complete inhibition of function, identical function, as well as enhancement of function. Embodiments of modulators of the invention include antibodies, peptides, oligonucleotides and small organic molecules including peptidomimetics.

The proteins of the present invention or their fragments comprising at least one epitope can be used to produce antibodies, both polyclonal and monoclonal, directed to epitopes corresponding to amino acid sequences disclosed herein. If polyclonal antibodies are desired, a selected mammal such as a mouse, rabbit, goat or horse is immunized with a protein of the present invention, or its fragment, or a mutant protein. Serum from the immunized animal is collected and treated according to known procedures. Serum polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion and also by other techniques such as direct transformation of B lymphocytes with oncogenic DNA or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); and U.S. Pat. Nos. 4,341,761; 4,399, 121; 4,427,783; 4,444,887; 4,452,570; 4,466,917; 4,472, 500; 4,491,632; and 4,493,890.

Panels of monoclonal antibodies produced against the antigen of interest, or fragment thereof, can be screened for various properties, i.e., for isotype, epitope, affinity, etc. Monoclonal antibodies are useful in purification, using immunoaffinity techniques, of the individual antigens which they are directed against. Alternatively, genes encoding the monoclonals of interest may be isolated from the hybridomas by PCR techniques known in the art and cloned and expressed in the appropriate vectors. The antibodies of this invention, whether polyclonal or monoclonal have additional utility in that they may be employed as reagents in immunoassays, RIA, ELISA, and the like. The antibodies of the invention can be labeled with an analytically detectable reagent such as a radioisotope, fluorescent molecule or enzyme.

An additional use of monoclonal antibodies is to treat various pathologies arising from overproduction or inappropriate production of SDMF. Such pathologies may include restenosis and atherosclerosis. A therapeutically effective amount of an SDMF-modulating monoclonal antibody is administered to a patient having a need to modulate SDMF activity.

Chimeric antibodies, in which non-human variable regions are joined or fused to human constant regions (see, e.g., Liu et al., *Proc. Natl Acad. Sci. USA*, 84, 3439 (1987)), may also be used in assays or therapeutically. Preferably, a therapeutic monoclonal antibody would be "humanized" as described in Jones et al., *Nature*, 321, 522 (1986); Verhoeyen et al., *Science*, 239, 1534 (1988); Kabat et al., *J. Immunol.*, 147, 1709 (1991); Queen et al., *Proc. Natl Acad. Sci. USA*, 86, 10029 (1989); Gorman et al., *Proc. Natl Acad. Sci. USA*, 88, 34181 (1991); and Hodgson et al., *Bio/Technology*, 9:, 421 (1991).

Another aspect of the invention is antisense oligonucleotides comprising a sequence which is capable of binding to the polynucleotides of the invention. Synthetic oligonucleotides or related antisense chemical structural analogs can be designed to recognize and specifically bind to and prevent transcription of a target nucleic acid encoding SDMF protein by those of ordinary skill in the art. See generally, Cohen, J. S., *Trends in Pharm. Sci.*, 10, 435 (1989) and Weintraub, H. M., *Scientific American*, January (1990) at page 40.

Another aspect of the invention is a method for assaying a medium for the presence of a substance that inhibits or otherwise modulates SDMF protein function by interfering with the binding of SDMF protein to binding partners. Examples include, but are not limited to, a cell surface receptor, soluble receptor, binding protein, antibody and any fragments thereof as well as fragments of SDMF protein. Other exemplary modulators of SDMF protein function include peptidomimetics of any of the peptides or proteins mentioned above or other small organic molecules.

A SDMF protein having the amino acid sequence of human SDMF (SEQ ID NO: 2) or a functional derivative thereof and SMC are provided in a chemotaxis assay chamber as described in Example 3, infra, or in any other migration assay known to those skilled in the art such as that described by Koyama et al. in *J. Biol. Chem.*, supra. A test substance which is suspected of modulating SDMF activity is added to either the SDMF or SMC, the chamber is incubated under conditions which permit the migration of SMC and the number of migrated and nonmigrated SMC counted. The result is compared to a control to determine the effect of the test substance.

A SDMF protein is provided having the amino acid sequence of human SDMF (SEQ ID NO: 2) or a functional derivative thereof together with a binding partner. The mixture is incubated with a test substance which is suspected of modulating SDMF activity, under conditions which permit the formation of a SDMF gene product/binding partner complex. An assay is performed for the presence of the complex, free SDMF protein or free binding partner and the result compared to a control to determine the effect of the test substance.

Modulation of SDMF function would be expected to have effects on SMC migration. Any modulators so identified would be expected to be useful as a therapeutic for the treatment and prevention of atherosclerosis, restenosis or other blood vessel pathologies where SMC migration is involved.

Further, most, if not all, SMC migration factors interact with specific receptor proteins. SDMF could be used to isolate proteins which interact with it and this interaction could be a target for interference. Inhibitors of protein-protein interactions between SDMF and other factors could lead to the development of pharmaceutical agents for the modulation of SDMF activity.

Methods to assay for protein-protein interactions, such as that of a SDMF gene product/binding partner complex, and to isolate proteins interacting with SDMF are known to those skilled in the art. Use of the methods discussed below enable one of ordinary skill in the art to accomplish these aims without undue experimentation.

The yeast two-hybrid system provides methods for detecting the interaction between a first test protein and a second test protein, in vivo, using reconstitution of the activity of a transcriptional activator. The method is disclosed in, e.g., U.S. Pat. No. 5,283,173; reagents are available from Clontech and Stratagene. Briefly, SDMF cDNA is fused to a Gal4 transcription factor DNA binding domain and expressed in yeast cells. cDNA library members obtained from cells of interest are fused to a transactivation domain of Gal4. cDNA clones which express proteins which can interact with SDMF will lead to reconstitution of Gal4 activity and transactivation of expression of a reporter gene such as Gal1-lacZ.

An alternative method is screening of λgt11, λZAP (Stratagene) or equivalent cDNA expression libraries with recombinant SDMF. Recombinant SDMF protein or fragments thereof are fused to small peptide tags such as FLAG, HSV or GST. The peptide tags can possess convenient phosphorylation sites for a kinase such as heart muscle creatine kinase or they can be biotinylated. Recombinant SDMF can be phosphorylated with $^{32}$[P] or used unlabeled and detected with streptavidin or antibodies against the tags. λgt11cDNA expression libraries are made from cells of interest and are incubated with the recombinant SDMF, washed and cDNA clones isolated which interact with SDMF. See, e.g., T. Maniatis et al, supra.

Another method is the screening of a mammalian expression library in which the cDNAs are cloned into a vector between a mammalian promoter and polyadenylation site and transiently transfected in COS or 293 cells followed by detection of the binding protein 48 hours later by incubation of fixed and washed cells with a labelled SDMF, preferably iodinated, and detection of bound SDMF by autoradiography (See Sims et al., *Science* 241, 585–589 (1988) and McMahan et al., *EMBO J.* 10, 2821–2832 (1991)). In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing SDMF bound to the plate. Cells which attach after washing are lysed and the plasmid DNA isolated, amplified in bacteria, and the cycle of transfection and panning repeated until a single cDNA clone is obtained (See Seed et al, *Proc. Natl. Acad. Sci. USA* 84, 3365 (1987) and Aruffo et al., *EMBO J.* 6, 3313 (1987)). If the binding protein is secreted, its cDNA can be obtained by a similar pooling strategy once a binding or neutralizing assay has been established for assaying supernatants from transiently transfected cells. General methods for screening supernatants are disclosed in Wong et al., *Science* 228, 810–815 (1985).

Another alternative method is isolation of proteins interacting with SDMF directly from cells. Fusion proteins of SDMF with GST or small peptide tags are made and immobilized on beads. Biosynthetically labeled or unlabeled protein extracts from the cells of interest are prepared, incubated with the beads and washed with buffer. Proteins interacting with SDMF are eluted specifically from the beads and analyzed by SDS-PAGE. Binding partner primary amino acid sequence data are obtained by microsequencing.

Another alternative method is immunoaffinity purification. Recombinant SDMF is incubated with labeled or unlabeled cell extracts and immunoprecipitated with anti-SDMF antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled SDMF is used to select peptides from a peptide library which interact with SDMF. Sequencing of the peptides leads to identification of consensus peptide sequences which might be found in interacting proteins.

SDMF binding partners identified by any of these methods or other methods which would be known to those of ordinary skill in the art as well as those putative binding partners discussed above can be used in the assay method of the invention. Assaying for the presence of SDMF/binding partner complex are accomplished by, for example, the yeast two-hybrid system, ELISA or immunoassays using antibodies specific for the complex. In the presence of test substances which interrupt or inhibit formation of SDMF/binding partner interaction, a decreased amount of complex will be determined relative to a control lacking the test substance.

Assays for free SDMF or binding partner are accomplished by, for example, ELISA or immunoassay using specific antibodies or by incubation of radiolabeled SDMF with cells or cell membranes followed by centrifugation or filter separation steps. In the presence of test substances which interrupt or inhibit formation of SDMF/binding partner interaction, an increased amount of free SDMF or free binding partner will be determined relative to a control lacking the test substance.

Another aspect of the invention is pharmaceutical compositions comprising an effective amount of SDMF protein of the invention and a pharmaceutically acceptable carrier. Pharmaceutical compositions of proteinaceous drugs of this invention are particularly useful for parenteral administration, i.e., subcutaneously, intramuscularly or intravenously. Optionally, the SDMF protein is surrounded by a membrane bound vesicle, such as a liposome.

The compositions for parenteral administration will commonly comprise a solution of the proteins of the invention or a cocktail thereof dissolved in an acceptable carrier, preferably an aqueous carrier. A variety of aqueous carriers may be employed, e.g., water, buffered water, 0.4% saline, 0.3% glycine and the like. These solutions are sterile and generally free of particulate matter. These solutions may be sterilized by conventional well-known sterilization techniques. The compositions may contain pharmaceutically acceptable auxiliary substances as required to approximate physiological conditions such as pH adjusting and buffering agents, etc. The concentration of the protein of the invention in such pharmaceutical formulation can vary widely, i.e., from less than about 0.5%, usually at or at least about 1% to as much as 15 or 20% by weight, and will be selected primarily based on fluid volumes, viscosities, etc. according to the particular mode of administration selected.

Thus, a pharmaceutical composition of the invention for intramuscular injection could be prepared to contain 1 mL sterile buffered water and 50 mg of a protein of the invention. Similarly, a pharmaceutical composition of the invention for intravenous infusion could be made up to contain 250 ml of sterile Ringer's solution and 150 mg of a protein of the invention. Actual methods for preparing parenterally administrable compositions are well known or will be apparent to those skilled in the art and are described in more detail in, e.g., *Remington's Pharmaceutical Science,* 15th ed., Mack Publishing Company, Easton, Pa.

The proteins described herein can be lyophilized for storage and reconstituted in a suitable carrier prior to use. This technique has been shown to be effective with conventional proteins and art-known lyophilization and reconstitution techniques can be employed.

The physician will determine the dosage of the present therapeutic agents which will be most suitable and it will vary with the form of administration and the particular compound chosen, and furthermore, it will vary with the particular patient under treatment. Generally, the physician will wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The therapeutic dosage will generally be from 1 to 10 milligrams per day and higher although it may be administered in several different dosage units.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance to the disease.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

Additionally, some diseases result from inherited defective genes. These genes can be detected by comparing the sequence of the defective gene with that of a normal one. Individuals carrying mutations in the SDMF gene may be detected at the DNA level by a variety of techniques. Nucleic acids used for diagnosis (genomic DNA, mRNA, etc.) may be obtained from a patient's cells, such as from blood, urine, saliva or tissue biopsy, e.g., chorionic villi sampling or removal of amniotic fluid cells and autopsy material. The genomic DNA may be used directly for detection or may be amplified enzymatically by using PCR, ligase chain reaction (LCR), strand displacement amplification (SDA), etc. prior to analysis. See, e.g., Saiki et al., *Nature*, 324, 163–166 (1986), Bej, et al., *Crit. Rev. Biochem. Molec. Biol.*, 26, 301–334 (1991), Birkenmeyer et al., *J. Virol. Meth.*, 35, 117–126 (1991), Van Brunt, J., *Bio/Technology*, 8, 291–294 (1990)). RNA or cDNA may also be used for the same purpose. As an example, PCR primers complementary to the nucleic acid of the instant invention can be used to identify and analyze SDMF mutations. For example, deletions and insertions can be detected by a change in size of the amplified product in comparison to the normal SDMF genotype. Point mutations can be identified by hybridizing amplified DNA to rabiolabeled SDMF RNA of the invention or alternatively, radiolabelled SDMF antisense DNA sequences of the invention. Perfectly matched sequences can be distinguished from mismatched duplexes by RNase A digestion or by differences in melting temperatures (Tm). Such a diagnostic would be particularly useful for prenatal and even neonatal testing.

In addition, point mutations and other sequence differences between the reference gene and "mutant" genes can be identified by yet other well-known techniques, e.g., direct DNA sequencing, single-strand conformational polymorphism. See Orita et al., *Genomics*, 5, 874–879 (1989). For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags. Cloned DNA segments may also be used as probes to. detect specific DNA segments. The sensitivity of this method is greatly enhanced when combined with PCR. The presence of nucleotide repeats may correlate to a causative change in SDMF activity or serve as marker for various polymorphisms.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures. See, e.g., Myers et al., *Science*, 230, 1242 (1985). In addition, sequence alterations, in particular small deletions, may be detected as changes in the migration pattern of DNA heteroduplexes in non-denaturing gel electrophoresis such as heteroduplex electrophoresis. See, e.g., Nagamine et al., *Am. J. Hum. Genet.*, 45, 337–339 (1989). Sequence changes at specific locations may also be revealed by nuclease protection assays, such as RNase and S1 protection or the chemical cleavage method as disclosed by Cotton et al. in *Proc. Natl. Acad. Sci. USA*, 85, 4397–4401 (1985).

Thus, the detection of a specific DNA sequence may be achieved by methods such as hybridization (e.g., heteroduplex electroporation, see, White et al., *Genomics*, 12, 301–306 (1992), RNAse protection (e.g., Myers et al., *Science*, 230, 1242 (1985)) chemical cleavage (e.g., Cotton et al., *Proc. Natl. Acad. Sci. USA*, 85, 4397–4401 (1985))), direct DNA sequencing, or the use of restriction enzymes, e.g., restriction fragment length polymorphisms (RFLP) in which variations in the number and size of restriction fragments can indicate insertions, deletions, presence of nucleotide repeats and any other mutation which creates or destroys an endonuclease restriction sequence. Southen blotting of genomic DNA may also be used to identify large, i.e., greater than 100 base pair deletions and insertions.

In addition to conventional gel electrophoresis and DNA sequencing, mutations such as microdeletions, aneuploidies, translocations and inversions, can also be detected by in situ analysis. See, e.g., Keller et al., DNA Probes, 2nd Ed., Stockton Press, New York, N.Y., U.S.A. (1993). That is, DNA or RNA sequences in cells can be analyzed for mutations without isolation and/or immobilization onto a membrane. Fluorescence in situ hybridization (FISH) is presently the most commonly applied method and numerous reviews of FISH have appeared. See, e.g., Trachuck et al., *Science*, 250, 559–562 (1990), and Trask et al., *Trends, Genet.*, 7, 149–154 (1991). Hence, by using nucleic acids based on the structure of the SDMF genes, one can develop diagnostic tests for genetic mutations.

In addition, some diseases are a result of, or are characterized by, changes in gene expression which can be detected by changes in the mRNA. Alternatively, the SDMF gene can be used as a reference to identify individuals expressing an increased or decreased level of SDMF protein, e.g., by Northern blotting or in situ hybridization.

Defining appropriate hybridization conditions is within the skill of the art. See, e.g., "Current Protocols in Mol. Biol." Vol. I & II, Wiley Interscience. Ausbel et al. (eds.) (1992). Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioisotopes, fluorescent dyes or enzymes capable of catalyzing the formation of a detectable product. As a general rule, the more stringent the hybridization conditions, the more closely related genes will be that are recovered.

The role of human SDMF in the regulation of SMC migration establishes yet another aspect of the invention which is gene therapy. "Gene therapy" means gene supplementation where an additional reference copy of a gene of interest is inserted into a patient's cells. As a result, the protein encoded by the reference gene corrects the defect and permits the cells to function normally, thus alleviating disease symptoms. The reference copy would be a wild-type form of the SDMF gene or a gene encoding a protein or peptide which modulates the activity of the endogenous SDMF.

Gene therapy of the present invention can occur in vivo or ex vivo. Ex vivo gene therapy requires the isolation and purification of patient cells, the introduction of a therapeutic gene and introduction of the genetically altered cells back into the patient. A replication-deficient virus such as a modified retrovirus can be used to introduce the therapeutic SDMF gene into such cells. For example, mouse Moloney leukemia virus (MMLV) is a well-known vector in clinical gene therapy trials. See, e.g., Boris-Lauerie et al., *Curr. Opin. Genet. Dev.*, 3, 102–109 (1993).

In contrast, in vivo gene therapy does not require isolation and purification of a patient's cells. The therapeutic gene is typically "packaged" for administration to a patient such as in liposomes or in a replication-deficient virus such as adenovirus as described by Berkner, K. L., in *Curr. Top. Microbiol. Immunol.*, 158, 39–66 (1992) or adeno-associated virus (AAV) vectors as described by Muzyczka, N., in *Curr. Top. Microbiol. Immunol.*, 158, 97–129 (1992)

and U.S. Pat. No. 5,252,479. Another approach is administration of "naked DNA" in which the therapeutic gene is directly injected into the bloodstream or muscle tissue. Another approach is administration of "naked DNA" in which the therapeutic gene is introduced into the target tissue by microparticle bombardment using gold particles coated with the DNA.

Cell types useful for gene therapy of the present invention include lymphocytes, hepatocytes, myoblasts, fibroblasts, any cell of the eye such as retinal cells, epithelial and endothelial cells. Transfection of pulmonary epithelial cells can occur via inhalation of a neubulized preparation of DNA vectors in liposomes, DNA-protein complexes or replication-deficient adenoviruses. See, e.g., U.S. Pat. No. 5,240,846.

Another aspect of the invention is transgenic, non-human mammals capable of expressing the polynucleotides of the invention in any cell. Transgenic, non-human animals may be obtained by transfecting appropriate fertilized eggs or embryos of a host with the polynucleotides of the invention or with mutant forms found in human diseases. See, e.g., U.S. Pat. Nos. 4,736,866; 5,175,385; 5,175,384 and 5,175,386. The resultant transgenic animal may be used as a model for the study of SDMF gene function. Particularly useful transgenic animals are those which display a detectable phenotype associated with the expression of the SDMF protein. Drug development candidates may then be screened for their ability to reverse or exacerbate the relevant phenotype.

The present invention will now be described with reference to the following specific, non-limiting examples.

EXAMPLE 1

Cloning of Human SDMF Full-length cDNA and Sequence Analysis

Rat SDMF protein was purified by the method of Koyama et al. in *J. Biol. Chem.*, supra. The purified 60 kDa protein was subjected to automated Edman degradation sequencing and found to contain a blocked N-terminus. Additional SDS-PAGE purified material was subjected to in situ tryptic digest and eluted peptides purified by microbore C18 reversed-phase chromatography. Edman sequencing of a tryptic peptide of experimental mass 1655.5 Da as determined by MALDI mass spectrometry was found to contain the sequence YDALEVFAGSGTSGQR (SEQ ID NO:3). Comparison of the rat SDMF amino acid sequence with the PIR database indicated an exact match to a 402 amino acid murine sequence of unknown function having Genbank accession number JH0403. This sequence was identified as p14 and the DNA and amino acid sequences were reported in Lecain et al., supra (SEQ ID NOs: 4 and 5). Based on these results, the heretofore unknown function of murine p14 was determined to be that of a smooth muscle cell-derived migration factor.

A search of a random cDNA sequence database consisting of short partial sequences known as expressed sequence tags (ESTs) with the murine p14 sequence disclosed many ESTs which encoded parts of the putative human homologue of p14 or SDMF. A cDNA containing an EST which matched the 5' end of the murine p14 cDNA sequence and which contained a start codon was selected and further sequenced (SEQ ID NO:1). This cDNA was originally isolated from a human fetal heart cDNA library in λZAP.

Sequence analysis of the SDMF cDNA revealed a 1,347 nucleotide open reading frame (SEQ ID NO:1) encoding a 449 amino acid protein with a predicted molecular mass of 49.4 kDa (SEQ ID NO:2), starting with an ATG at position 94 and terminating with a TGA at position 1441.

The murine p14 DNA sequence (SEQ ID NO:4) reported by Lecain et al. was determined by Takahara et al., supra, to omit two guanosine residues. One additional residue was located between nucleotides 1213 and 1214 and the other between nucleotides 1375 and 1376 of the sequence published by Lecain et al. The corrected murine p14 DNA and amino acid sequences are shown in SEQ ID NOs: 6 and 7, respectively.

Alignment of the deduced amino acid sequence of human SDMF with the corrected murine p14 sequence was accomplished using the GCG program Bestfit. The overall amino acid identity was 85% with 5 gaps and is shown in FIG. 1 (top, human SDMF; bottom, murine p14). Both protein sequences encode two repeats (36–145 and 158–269 of the murine sequence) of a region homologous to a domain found in the complement proteins C1r and C1s and the secreted proteins human bone morphogenic protein-1, AS antigen from Xenopus, bovine acidic seminal fluid precursor protein and porcine sperm adhesin proteins AWN, AQN-1 and -3.

A search of the GenEMBL database with the murine p14 amino acid sequence (SEQ ID NO:5) disclosed a 449 amino acid human procollagen C-proteinase enhancer protein (PCOLCE), accession number L33799 (SEQ ID NOs: 8 and 9), having 90.1% identity. PCOLCE was reported in Takahara et al., supra. Alignment of the deduced amino acid sequence of human SDMF (SEQ ID NO:2) with the human PCOLCE sequence (SEQ ID NO:9) was accomplished using the GCG program Bestfit. The overall amino acid identity was 99% with zero gaps and is shown in FIG. 2 (top, human SDMF; bottom, human PCOLCE).

EXAMPLE 2

Expression of Human SDMF

The putative human SDMF cDNA was isolated from its cloning vector (Bluescript) by digestion with EcoR1(5' end) and Kpn1 (3' end) and inserted into the mammalian expression vector pCDN (Aiyar et al., *Molecular and Cellular Biochemistry* 131, 75–86 (1994)). 60 ug of this vector DNA was transfected into $8 \times 10^6$ COS cells plated the previous day into a 150 mm flask using the DEAE dextran/chloroquine method of Maniatis et al, supra, followed by a 10% DMSO shock (eg Maniatis et al). Cells were left in 10% FBS/DMEM for 24 h post transfection at which time serum-containing medium was removed, cells were washed twice with PBS and 15 mL of serum-free medium with nucleosides was added. Media was harvested 48 h and 120 h later, centrifuged to remove cell debris and the pH adjusted to ca. 8.0 with 7.5% sodium bicarbonate.

Large scale COS transfections were performed essentially identically using 1 liter cell factories seeded 1 day before transfection at a density of 20,000 cells/cm$^2$ and 1.8 mg/mL of DNA in DEAE/dextran followed after 4 h by 10% DMSO and incubation in serum free media for 3 days.

EXAMPLE 3

Bioactivity of Human SDMF

The bioactivity of human SDMF expressed in COS cells was demonstrated in vitro in a rat aortic smooth muscle cell migration model. This model was reported by Hidaka et al. in *Atherosclerosis* 95, 87–94 (1992). Rat aortic smooth muscle cells (RASMC) were suspended in Dulbecco's modified Eagle's medium (DMEM) supplemented with 0.2% bovine serum albumin (BSA) at a concentration of $2.5 \times 10^6$/mL. In the assay, 0.2 mL of RASMCs was placed in the upper compartment of the assay chamber. The lower compartment of the chamber contained 0.6 mL of DMEM supplemented with 0.2% BSA. Human SDMF which was purified to near homogeneity from COS cell culture supernatant was either coated on the lower surface of the filter or added to the lower compartment. RASMC were subjected to either platelet-derived growth factor(PDGF)at a concentration (1 nM) which induces maximum smooth muscle cell migration (control) or various concentrations of purified SDMF. Incubation was at 37° C. in an atmosphere of 95% air and 5% $CO_2$ for 20 hours. After incubation, nonmigrated cells on the upper surface were scraped gently and washed with PBS three times. The filters were fixed and stained with Giemsa stain. The number of SMC that had migrated to the lower surface of the filters was determined microscopically and one randomly chosen high-power field (HPF) was counted per filter. Experiments were performed in triplicate. The results in FIG. 1 show that purified SDMF enhanced the migration of rat smooth muscle cells dose dependently and its maximum activity was at least 4–5 times that of PDGF which is consistent with published observations by Koyama et al., *J. Biol. Chem.*, supra.

The present invention may be embodied in other specific forms without departing from the spirit or essential attributes thereof, and, accordingly, reference should be made to the appended claims, rather than to the foregoing specification, as indicating the scope of the invention.

We claim:

1. A method for assaying a test substance for the ability to modulate Smooth muscle cell-derived migration factor (SDMF) activity comprising the steps of:

(a) providing a SDMF protein having the amino acid sequence of SDMF as shown in SEQ ID NO:2 in a first compartment of a chamber and smooth muscle cells (SMC) in a second compartment of the chamber, wherein the first and second compartment are separated by a filter;

(b) adding the test substance to either the SDMF or SMC;

(c) incubating the chamber under conditions which permit the migratiom of SMC;

(d) counting the number of migrated and nonmigrated SMC; and (e) comparing to a control to determine the effect of the test substance as a modulator of SDMF activity.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1537 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATTATCCTGC TGCTGCCGCC ACCGCTGCTG CTGCTCTGCA AAATTCAGCT GCTGCCTCTG      60

TCTTGAGGAC CCCAGCGCCT TTCCCCCGGG GCCATGCTGC CTGCAGCCAC AGCCTCCCTC     120

CTGGGGCCCC TCCTCACTGC CTGCGCCCTG CTGCCTTTTG CCCAGGGCCA GACCCCCAAC     180

TACACCAGAC CCGTGTTCCT GTGCGGAGGG GATGTGAAGG GGGAATCAGG TTACGTGGCA     240

AGTGAGGGGT TCCCCAACCT CTACCCCCCT AATAAGGAGT GCATCTGGAC CATAACGGTC     300

CCCGAGGGCC AGACTGTGTC CCTCTCATTC CGAGTCTTCG ACCTGGAGCT GCACCCCGCC     360

TGCCGCTACG ATGCTCTGGA GGTCTTCGCT GGGTCTGGGA CTTCCGGCCA GCGGCTCGGA     420

CGCTTTTGTG GGACCTTCCG GCCTGCGCCC CTAGTCGCCC CCGGCAACCA GGTGACCCTG     480

AGGATGACGA CGGATGAGGG CACAGGAGGA CGAGGCTTCC TGCTCTGGTA CAGCGGGCGG     540

GCCACCTCGG GCACTGAGCA CCAATTTTGC GGGGGCGGC TGGAGAAGGC CCAGGGAACC     600

CTGACCACGC CCAACTGGCC CGAGTCCGAT TACCCCCCGG GCATCAGCTG TTCCTGGCAC     660

ATCATCGCGC CCCCGGACCA GGTCATCGCG CTGACCTTCG AGAAGTTTGA CCTGGAGCCG     720

GACACCTACT GCCGCTATGA CTCGGTCAGC GTGTTCAACG GAGCCGTGAG CGACGACTCC     780

CGGAGGCTGG GGAAGTTCTG CGGCGACGCA GTCCCGGGCT CCATCTCCTC CGAAGGGAAT     840

GAACTCCTCG TCCAGTTCGT CTCAGATCTC AGTGTCACCG CTGATGGCTT CTCAGCCTCC     900

TACAAGACCC TGCCGCGGGG CACTGCCAAA GAAGGGCAAG GGCCCGGCCC CAAACGGGGA     960

ACTGAGCCTA AAGTCAAGCT GCCCCCCAAG TCCCAACCTC CGGAGAAAAC AGAGGAATCT    1020

CCTTCAGCCC CTGATGCACC CACCTGCCCA AAGCAGTGCC GCCGGACAGG CACCTTGCAG    1080

AGCAACTTCT GTGCCAGCAG CCTTGTGGTG ACTGCGACAG TGAAGTCCAT GGTTCGGGAG    1140

CCAGGGGAGG GCCTTGCCGT GACTGTCAGT CTTATTGGTG CTTATAAAAC TGGAGGACTG    1200
```

```
GACCTGCCTT CTCCACCCAC TGGTGCCTCC CTGAAGTTTT ACGTGCCTTG CAAGCAGTGC      1260

CCCCCCATGA AGAAAGGAGT CAGTTATCTG CTGATGGGCC AGGTAGAAGA GAACAGAGGC      1320

CCCGTCCTTC CTCCAGAGAG CTTTGTGGTT CTCCACCGGC CCAACCAGGA CCAGATCCTC      1380

ACCAACCTAA GCAAGAGGAA GTGCCCCTCT CAACCTGTGC GGGCTGCTGC GTCCCAGGAC      1440

TGAGACGCAG GCCAGCCCCG GCCCCTAGCC CTCAGGCCTT CTTTCTTATC CAAATAAATG      1500

TTTCTTAATG AAAAAAAAAA AAAAAAAAAA AAAAAA                                1537
```

(2) INFORMATION FOR SEQ ID NO:2:

(i) SEQUENCE CHARACTERISTICS:
        (A) LENGTH: 449 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Leu Pro Ala Ala Thr Ala Ser Leu Leu Gly Pro Leu Leu Thr Ala
 1               5                  10                  15

Cys Ala Leu Leu Pro Phe Ala Gln Gly Gln Thr Pro Asn Tyr Thr Arg
                20                  25                  30

Pro Val Phe Leu Cys Gly Gly Asp Val Lys Gly Glu Ser Gly Tyr Val
            35                  40                  45

Ala Ser Glu Gly Phe Pro Asn Leu Tyr Pro Pro Asn Lys Glu Cys Ile
        50                  55                  60

Trp Thr Ile Thr Val Pro Glu Gly Gln Thr Val Ser Leu Ser Phe Arg
65                  70                  75                  80

Val Phe Asp Leu Glu Leu His Pro Ala Cys Arg Tyr Asp Ala Leu Glu
                85                  90                  95

Val Phe Ala Gly Ser Gly Thr Ser Gly Gln Arg Leu Gly Arg Phe Cys
            100                 105                 110

Gly Thr Phe Arg Pro Ala Pro Leu Val Ala Pro Gly Asn Gln Val Thr
        115                 120                 125

Leu Arg Met Thr Thr Asp Glu Gly Thr Gly Gly Arg Gly Phe Leu Leu
    130                 135                 140

Trp Tyr Ser Gly Arg Ala Thr Ser Gly Thr Glu His Gln Phe Cys Gly
145                 150                 155                 160

Gly Arg Leu Glu Lys Ala Gln Gly Thr Leu Thr Thr Pro Asn Trp Pro
                165                 170                 175

Glu Ser Asp Tyr Pro Pro Gly Ile Ser Cys Ser Trp His Ile Ile Ala
            180                 185                 190

Pro Pro Asp Gln Val Ile Ala Leu Thr Phe Glu Lys Phe Asp Leu Glu
        195                 200                 205

Pro Asp Thr Tyr Cys Arg Tyr Asp Ser Val Ser Val Phe Asn Gly Ala
    210                 215                 220

Val Ser Asp Asp Ser Arg Arg Leu Gly Lys Phe Cys Gly Asp Ala Val
225                 230                 235                 240

Pro Gly Ser Ile Ser Ser Glu Gly Asn Glu Leu Leu Val Gln Phe Val
                245                 250                 255

Ser Asp Leu Ser Val Thr Ala Asp Gly Phe Ser Ala Ser Tyr Lys Thr
            260                 265                 270

Leu Pro Arg Gly Thr Ala Lys Glu Gly Gln Gly Pro Gly Pro Lys Arg
        275                 280                 285
```

```
        Gly Thr Glu Pro Lys Val Lys Leu Pro Pro Lys Ser Gln Pro Pro Glu
            290                 295                 300

Lys Thr Glu Glu Ser Pro Ser Ala Pro Asp Ala Pro Thr Cys Pro Lys
        305                 310                 315                 320

Gln Cys Arg Arg Thr Gly Thr Leu Gln Ser Asn Phe Cys Ala Ser Ser
                        325                 330                 335

Leu Val Val Thr Ala Thr Val Lys Ser Met Val Arg Glu Pro Gly Glu
                    340                 345                 350

Gly Leu Ala Val Thr Val Ser Leu Ile Gly Ala Tyr Lys Thr Gly Gly
                355                 360                 365

Leu Asp Leu Pro Ser Pro Pro Thr Gly Ala Ser Leu Lys Phe Tyr Val
            370                 375                 380

Pro Cys Lys Gln Cys Pro Pro Met Lys Lys Gly Val Ser Tyr Leu Leu
        385                 390                 395                 400

Met Gly Gln Val Glu Glu Asn Arg Gly Pro Val Leu Pro Pro Glu Ser
                        405                 410                 415

Phe Val Val Leu His Arg Pro Asn Gln Asp Gln Ile Leu Thr Asn Leu
                    420                 425                 430

Ser Lys Arg Lys Cys Pro Ser Gln Pro Val Arg Ala Ala Ala Ser Gln
                435                 440                 445

Asp
```

(2) INFORMATION FOR SEQ ID NO:3:

(i) SEQUENCE CHARACTERISTICS:
       (A) LENGTH: 16 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

```
        Tyr Asp Ala Leu Glu Val Phe Ala Gly Ser Gly Thr Ser Gly Gln Arg
        1               5                   10                  15
```

(2) INFORMATION FOR SEQ ID NO:4:

(i) SEQUENCE CHARACTERISTICS:
       (A) LENGTH: 1504 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:4:

```
CTGAACTCAG CTGCTGCTGC TTCCACCACT TCCCCCCTAC ACAATGCTGC CTGCTGCCCT    60

AACCTCCTTT CTGGGGCCAT TCCTTTTGGC CTGGGTGCTG CCTCTTGCCC GAGGCCAGAC   120

CCCCAACTAC ACGAGACCTG TGTTCCTGTG CGGAGGGGAC GTGACCGGGG AGTCAGGTTA   180

CGTGGCAAGT GAGGGTTTCC CCAACCTCTA CCCCCCAAAC AAGAAGTGCA TCTGGACAAT   240

TACGGTGCCC GAGGGGCAGA CTGTGTCCCT GTCCTTCCGA GTGTTCGATA TGGAGCTCCA   300

CCCTTCCTGC CGCTACGATG CTCTGGAGGT CTTTGCTGGC TCTGGCACCT CAGGCCAGCG   360

ACTTGGACGC TTCTGCGGCA CCTTCAGGCC TGCACCTGTA GTCGCACCTG CAACCAAGT    420

GACTTTAAGG ATGACAACTG ACGAGGGCAC CGGGGGACGA GGCTTCCTGC TCTGGTACAG   480

CGGCCGGGCC ACTTCGGGCA CTGAGCACCA GTTTTGTGGG GGCGGATGG  AGAAGGCGCA   540

GGGAACCTTG ACCACGCCCA ACTGGCCTGA GTCGTATTAC CCACCAGGCA TCAGCTGTTC   600
```

```
CTGGCACATC ATTGCACCCT CAAACCAGGT GATCATGCTA ACCTTTGGGA AGTTTGATGT      660

GGAGCCTGAC ACGTACTGCC GATATGACTC TGTCAGTGTG TTTAACGGAG CTGTGAGTGA      720

CGACTCAAAG AGGCTGGGGA AATTTTGCGG AGACAAGGCC CCTAGCCCCA TCTCTTCTGA      780

AGGGAACGAG CTCCTGGTCC AGTTTGTATC AGATCTCAGT GTCACCGCAG ATGGCTTCTC      840

AGCCTCCTAC AGGACCCTGC CACGGGATGC CGTAGAGAAG GAGTCAGCCC TGAGTCCAGG      900

GGAGGACGTA CAGCGTGGTC CCCAGTCCCG CTCTGACCCT AAGACAGGAA CTGGGCCCAA      960

AGTCAAACCA CCCACTAAAC CTAAATCCCA ACCTGCAGAG ACACCAGAGG CTTCCCCTGC     1020

TACCCAGGCA ACCCCAGTGG CCCCAGCTGC CCCCAGCATC ACCTGCCCAA AGCAGTACAA     1080

GCGGTCAGGC ACCTTGCAGA GCAACTTCTG TTCCAGTAGC CTAGTGGTGA CAGGAACAGT     1140

GAAGACCATG GTCCGGGGCC CCGGGGAAGG CCTCACTGTC ACTGTCAGTC TCCTTGGTGT     1200

CTACAAAACC GGAGACTGGA CCTGCCCTCT CCGCCCAGTG GCACCTCTCT GAAGTTGTAT     1260

GTGCCCTGCA GGCAGATGCC CCCCATGAAG AAAGGAGCCA GTTATCTGCT GATGGGTCAG     1320

GTGGAAGAAA ACAGAGGCCC CATCCTTCCT CCAGAGAGCT TCGTGGTTCT CTACAGTCCA     1380

ACCAGGACCA GATCCTCAAT AACCTAAGCA AGAGGAAGTG TCCCTCCCAA CCTAGGACAG     1440

CTGCCTGATG TCCTAGCCAG ATTACAGCCT CAGAGCTCAT CCAATAAATG TTTCTTGACT     1500

CAAA                                                                 1504
```

(2) INFORMATION FOR SEQ ID NO:5:

(i) SEQUENCE CHARACTERISTICS:
        (A) LENGTH: 401 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Leu Pro Ala Ala Leu Thr Ser Phe Leu Gly Pro Phe Leu Leu Ala
 1               5                  10                  15

Trp Val Leu Pro Leu Ala Arg Gly Gln Thr Pro Asn Tyr Thr Arg Pro
                20                  25                  30

Val Phe Leu Cys Gly Gly Asp Val Thr Gly Glu Ser Gly Tyr Val Ala
            35                  40                  45

Ser Glu Gly Phe Pro Asn Leu Tyr Pro Pro Asn Lys Lys Cys Ile Trp
    50                  55                  60

Thr Ile Thr Val Pro Glu Gly Gln Thr Val Ser Leu Ser Phe Arg Val
65                  70                  75                  80

Phe Asp Met Glu Leu His Pro Ser Cys Arg Tyr Asp Ala Leu Glu Val
                85                  90                  95

Phe Ala Gly Ser Gly Thr Ser Gly Gln Arg Leu Gly Arg Phe Cys Gly
            100                 105                 110

Thr Phe Arg Pro Ala Pro Val Val Ala Pro Gly Asn Gln Val Thr Leu
        115                 120                 125

Arg Met Thr Thr Asp Glu Gly Thr Gly Gly Arg Gly Phe Leu Leu Trp
    130                 135                 140

Tyr Ser Gly Arg Ala Thr Ser Gly Thr Glu His Gln Phe Cys Gly Gly
145                 150                 155                 160

Arg Met Glu Lys Ala Gln Gly Thr Leu Thr Thr Pro Asn Trp Pro Glu
                165                 170                 175
```

```
            Ser Tyr Tyr Pro Pro Gly Ile Ser Cys Ser Trp His Ile Ile Ala Pro
                        180                 185                 190

Ser Asn Gln Val Ile Met Leu Thr Phe Gly Lys Phe Asp Val Glu Pro
                    195                 200                 205

Asp Thr Tyr Cys Arg Tyr Asp Ser Val Ser Val Phe Asn Gly Ala Val
                210                 215                 220

Ser Asp Ser Lys Arg Leu Gly Lys Phe Cys Gly Asp Lys Ala Pro
            225                 230                 235                 240

Ser Pro Ile Ser Ser Glu Gly Asn Glu Leu Leu Val Gln Phe Val Ser
                            245                 250                 255

Asp Leu Ser Val Thr Ala Asp Gly Phe Ser Ala Ser Tyr Arg Thr Leu
                        260                 265                 270

Pro Arg Asp Ala Val Glu Lys Glu Ser Ala Leu Ser Pro Gly Glu Asp
                    275                 280                 285

Val Gln Arg Gly Pro Gln Ser Arg Ser Asp Pro Lys Thr Gly Thr Gly
                290                 295                 300

Pro Lys Val Lys Pro Pro Thr Lys Pro Lys Ser Gln Pro Ala Glu Thr
            305                 310                 315                 320

Pro Glu Ala Ser Pro Ala Thr Gln Ala Thr Pro Val Ala Pro Ala Ala
                            325                 330                 335

Pro Ser Ile Thr Cys Pro Lys Gln Tyr Lys Arg Ser Gly Thr Leu Gln
                        340                 345                 350

Ser Asn Phe Cys Ser Ser Ser Leu Val Val Thr Gly Thr Val Lys Thr
                    355                 360                 365

Met Val Arg Gly Pro Gly Glu Gly Leu Thr Val Thr Val Ser Leu Leu
                370                 375                 380

Gly Val Tyr Lys Thr Gly Asp Trp Thr Cys Pro Leu Arg Pro Val Ala
            385                 390                 395                 400

Pro (2) INFORMATION FOR SEQ ID NO:6:

(i) SEQUENCE CHARACTERISTICS:
          (A) LENGTH: 1506 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:6:

CTGAACTCAG CTGCTGCTGC TTCCACCACT TCCCCCCTAC ACAATGCTGC CTGCTGCCCT      60

AACCTCCTTT CTGGGGCCAT TCCTTTTGGC CTGGGTGCTG CCTCTTGCCC GAGGCCAGAC     120

CCCCAACTAC ACGAGACCTG TGTTCCTGTG CGGAGGGGAC GTGACCGGGG AGTCAGGTTA     180

CGTGGCAAGT GAGGGTTTCC CCAACCTCTA CCCCCCAAAC AAGAAGTGCA TCTGGACAAT     240

TACGGTGCCC GAGGGGCAGA CTGTGTCCCT GTCCTTCCGA GTGTTCGATA TGGAGCTCCA     300

CCCTTCCTGC CGCTACGATG CTCTGGAGGT CTTTGCTGGC TCTGGCACCT CAGGCCAGCG     360

ACTTGGACGC TTCTGCGGCA CCTTCAGGCC TGCACCTGTA GTCGCACCTG GCAACCAAGT     420

GACTTTAAGG ATGACAACTG ACGAGGGCAC CGGGGGACGA GGCTTCCTGC TCTGGTACAG     480

CGGCCGGGCC ACTTCGGGCA CTGAGCACCA GTTTTGTGGG GGCGGATGG AGAAGGCGCA      540

GGGAACCTTG ACCACGCCCA ACTGGCCTGA GTCGTATTAC CCACCAGGCA TCAGCTGTTC     600

CTGGCACATC ATTGCACCCT CAAACCAGGT GATCATGCTA ACCTTTGGGA AGTTTGATGT     660

GGAGCCTGAC ACGTACTGCC GATATGACTC TGTCAGTGTG TTTAACGGAG CTGTGAGTGA     720
```

-continued

```
CGACTCAAAG AGGCTGGGGA AATTTTGCGG AGACAAGGCC CCTAGCCCCA TCTCTTCTGA    780

AGGGAACGAG CTCCTGGTCC AGTTTGTATC AGATCTCAGT GTCACCGCAG ATGGCTTCTC    840

AGCCTCCTAC AGGACCCTGC CACGGGATGC CGTAGAGAAG GAGTCAGCCC TGAGTCCAGG    900

GGAGGACGTA CAGCGTGGTC CCCAGTCCCG CTCTGACCCT AAGACAGGAA CTGGGCCCAA    960

AGTCAAACCA CCCACTAAAC CTAAATCCCA ACCTGCAGAG ACACCAGAGG CTTCCCCTGC   1020

TACCCAGGCA ACCCCAGTGG CCCCAGCTGC CCCCAGCATC ACCTGCCCAA AGCAGTACAA   1080

GCGGTCAGGC ACCTTGCAGA GCAACTTCTG TTCCAGTAGC CTAGTGGTGA CAGGAACAGT   1140

GAAGACCATG GTCCGGGGCC CCGGGGAAGG CCTCACTGTC ACTGTCAGTC TCCTTGGTGT   1200

CTACAAAACC GGAGGACTGG ACCTGCCCTC TCCGCCCAGT GGCACCTCTC TGAAGTTGTA   1260

TGTGCCCTGC AGGCAGATGC CCCCCATGAA GAAAGGAGCC AGTTATCTGC TGATGGGTCA   1320

GGTGGAAGAA AACAGAGGCC CCATCCTTCC TCCAGAGAGC TTCGTGGTTC TCTACAGGTC   1380

CAACCAGGAC CAGATCCTCA ATAACCTAAG CAAGAGGAAG TGTCCCTCCC AACCTAGGAC   1440

AGCTGCCTGA TGTCCTAGCC AGATTACAGC CTCAGAGCTC ATCCAATAAA TGTTTCTTGA   1500

CTCAAA                                                              1506
```

(2) INFORMATION FOR SEQ ID NO:7:

(i) SEQUENCE CHARACTERISTICS:
      (A) LENGTH: 468 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:7:

```
Met Leu Pro Ala Ala Leu Thr Ser Phe Leu Gly Pro Phe Leu Leu Ala
 1               5                  10                  15

Trp Val Leu Pro Leu Ala Arg Gly Gln Thr Pro Asn Tyr Thr Arg Pro
                20                  25                  30

Val Phe Leu Cys Gly Gly Asp Val Thr Gly Glu Ser Gly Tyr Val Ala
            35                  40                  45

Ser Glu Gly Phe Pro Asn Leu Tyr Pro Pro Asn Lys Lys Cys Ile Trp
        50                  55                  60

Thr Ile Thr Val Pro Glu Gly Gln Thr Val Ser Leu Ser Phe Arg Val
65                  70                  75                  80

Phe Asp Met Glu Leu His Pro Ser Cys Arg Tyr Asp Ala Leu Glu Val
                85                  90                  95

Phe Ala Gly Ser Gly Thr Ser Gly Gln Arg Leu Gly Arg Phe Cys Gly
            100                 105                 110

Thr Phe Arg Pro Ala Pro Val Val Ala Pro Gly Asn Gln Val Thr Leu
        115                 120                 125

Arg Met Thr Thr Asp Glu Gly Thr Gly Arg Gly Phe Leu Leu Trp
            130                 135                 140

Tyr Ser Gly Arg Ala Thr Ser Gly Thr Glu His Gln Phe Cys Gly Gly
145                 150                 155                 160

Arg Met Glu Lys Ala Gln Gly Thr Leu Thr Thr Pro Asn Trp Pro Glu
                165                 170                 175

Ser Tyr Tyr Pro Pro Gly Ile Ser Cys Ser Trp His Ile Ile Ala Pro
            180                 185                 190

Ser Asn Gln Val Ile Met Leu Thr Phe Gly Lys Phe Asp Val Glu Pro
        195                 200                 205
```

```
Asp Thr Tyr Cys Arg Tyr Asp Ser Val Ser Val Phe Asn Gly Ala Val
    210                 215                 220

Ser Asp Asp Ser Lys Arg Leu Gly Lys Phe Cys Gly Asp Lys Ala Pro
225                 230                 235                 240

Ser Pro Ile Ser Ser Glu Gly Asn Glu Leu Leu Val Gln Phe Val Ser
                245                 250                 255

Asp Leu Ser Val Thr Ala Asp Gly Phe Ser Ala Ser Tyr Arg Thr Leu
            260                 265                 270

Pro Arg Asp Ala Val Glu Lys Glu Ser Ala Leu Ser Pro Gly Glu Asp
        275                 280                 285

Val Gln Arg Gly Pro Gln Ser Arg Ser Asp Pro Lys Thr Gly Thr Gly
    290                 295                 300

Pro Lys Val Lys Pro Pro Thr Lys Pro Lys Ser Gln Pro Ala Glu Thr
305                 310                 315                 320

Pro Glu Ala Ser Pro Ala Thr Gln Ala Thr Pro Val Ala Pro Ala Ala
                325                 330                 335

Pro Ser Ile Thr Cys Pro Lys Gln Tyr Lys Arg Ser Gly Thr Leu Gln
            340                 345                 350

Ser Asn Phe Cys Ser Ser Ser Leu Val Val Thr Gly Thr Val Lys Thr
        355                 360                 365

Met Val Arg Gly Pro Gly Glu Gly Leu Thr Val Thr Val Ser Leu Leu
    370                 375                 380

Gly Val Tyr Lys Thr Gly Gly Leu Asp Leu Pro Ser Pro Pro Ser Gly
385                 390                 395                 400

Thr Ser Leu Lys Leu Tyr Val Pro Cys Arg Gln Met Pro Pro Met Lys
                405                 410                 415

Lys Gly Ala Ser Tyr Leu Leu Met Gly Gln Val Glu Glu Asn Arg Gly
            420                 425                 430

Pro Ile Leu Pro Pro Glu Ser Phe Val Val Leu Tyr Arg Ser Asn Gln
        435                 440                 445

Asp Gln Ile Leu Asn Asn Leu Ser Lys Arg Lys Cys Pro Ser Gln Pro
    450                 455                 460

Arg Thr Ala Ala
465
```

(2) INFORMATION FOR SEQ ID NO:8:

(i) SEQUENCE CHARACTERISTICS:
        (A) LENGTH: 1480 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
CTCTGCAAAA TTCAGCTGCT GCCTCTGTCT TGAGGACCCC AGCGCCTTTC CCCCGGGGCC    60

ATGCTGCCTG CAGCCACAGC CTCCCTCCTG GGGCCCCTCC TCACTGCCTG CGCCCTGCTG   120

CCTTTTGCCC AGGGCCAGAC CCCCAACTAC ACCAGACCCG TGTTCCTGTG CGGAGGGGAT   180

GTGAAGGGGG AATCAGGTTA CGTGGCAAGT GAGGGGTTCC CCAACTCCTA CCCCCCTAAT   240

AAGGAGTGCA TCTGGACCAT AACGGTCCCC GAGGGCCAGA CTGTGTCCCT CTCATTCCGA   300

GTCTTCGACC TGGAGCTGCA CCCCGCCTGC CGCTACGATG CTCTGGAGGT CTTCGCTGGG   360

TCTGGGACTT CCGGCCAGCG GCTCGGACGC TTTTGTGGGA CCTTCCGGCC TGCGCCCCTA   420

GTCGCCCCCG GCAACCAGGT GACCCTGAGG ATGACGACGG ATGAGGGCAC AGGAGGACGA   480
```

```
GGCTTCCTGC TCTGGTACAG CGGGCGGGCC ACCTCGGGCT CTGAGCACCA ATTTTGCGGG         540

GGGCGGCTGG AGAAGGCCCA GGGAACCCTG ACCACGCCCA ACTGGCCCGA GTCCGATTAC         600

CCCCCGGGCA TCAGCTGTTC CTGGCACATC ATCGCGCCCC CGGACCAGGT CATCGCGCTG         660

ACCTTCGAGA AGTTTGACCT GGAGCCGGAC ACCTACTGCC GCTATGACTC GGTCAGCGTC         720

TTCAACGGAG CCGTGAGCGA CGACTCCCGG AGGCTGGGGA AGTTCTGCGG CGACGCAGTC         780

CCGGGCTCCA TCTCCTCCGA AGGGAATGAA CTCCTCGTCC AGTTCGTCTC AGATCTCAGT         840

GTCACCGCTG ATGGCTTCTC AGCCTCCTAC AAGACCCTGC CGCGGGGCAC TGCCAAAGAA         900

GGGCAAGGGC CCGGCCCCAA ACGGGGAACT GAGCCTAAAG TCAAGCTGCC CCCCAAGTCC         960

CAACCTCCGG AGAAAACAGA GGAATCTCCT TCAGCCCCTG ATGCACCCAC CTGCCCAAAG        1020

CAGTGCCGCC GGACAGGCAC CTTGCAGAGC AACTTCTGTG CCAGCAGCCT TGTGGTGACT        1080

GCGACAGTGA AGTCCATGGT TCGGGAGCCA GGGGAGGGCC TTGCCGTGAC TGTCAGTCTT        1140

ATTGGTGCTT ATAAAACTGG AGGACTGGAC CTGCCAACTC CACCCACTGG TGCCTCCCTG        1200

AAGTTTTACG TGCCTTGCAA GCAGTGCCCC CCCATGAAGA AAGGAGTCAG TTATCTGCTG        1260

ATGGGCCAGG TAGAAGAGAA CAGAGGCCCC GTCCTTCCTC CAGAGAGCTT TGTGGTTCTC        1320

CACCGGCCCA ACCAGGACCA GATCCTCACC AACCTAAGCA AGAGGAAGTG CCCCTCTCAA        1380

CCTGTGCGGG CTGCTGCGTC CCAGGACTGA GACGCAGGCC AGCCCCGGCC CCTAGCCCTC        1440

AGGCCTCTCT TCTTATCCAA ATAAATGTTT CTTAATGAAA                              1480
```

(2) INFORMATION FOR SEQ ID NO:9:

(i) SEQUENCE CHARACTERISTICS:
        (A) LENGTH: 449 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Leu Pro Ala Ala Thr Ala Ser Leu Leu Gly Pro Leu Leu Thr Ala
 1               5                  10                  15

Cys Ala Leu Leu Pro Phe Ala Gln Gly Gln Thr Pro Asn Tyr Thr Arg
            20                  25                  30

Pro Val Phe Leu Cys Gly Gly Asp Val Lys Gly Glu Ser Gly Tyr Val
        35                  40                  45

Ala Ser Glu Gly Phe Pro Asn Ser Tyr Pro Pro Asn Lys Glu Cys Ile
    50                  55                  60

Trp Thr Ile Thr Val Pro Glu Gly Gln Thr Val Ser Leu Ser Phe Arg
65                  70                  75                  80

Val Phe Asp Leu Glu Leu His Pro Ala Cys Arg Tyr Asp Ala Leu Glu
                85                  90                  95

Val Phe Ala Gly Ser Gly Thr Ser Gly Gln Arg Leu Gly Arg Phe Cys
            100                 105                 110

Gly Thr Phe Arg Pro Ala Pro Leu Val Ala Pro Gly Asn Gln Val Thr
        115                 120                 125

Leu Arg Met Thr Thr Asp Glu Gly Thr Gly Gly Arg Gly Phe Leu Leu
    130                 135                 140

Trp Tyr Ser Gly Arg Ala Thr Ser Gly Ser Glu His Gln Phe Cys Gly
145                 150                 155                 160

Gly Arg Leu Glu Lys Ala Gln Gly Thr Leu Thr Thr Pro Asn Trp Pro
                165                 170                 175
```

```
Glu Ser Asp Tyr Pro Pro Gly Ile Ser Cys Ser Trp His Ile Ile Ala
            180             185             190

Pro Pro Asp Gln Val Ile Ala Leu Thr Phe Glu Lys Phe Asp Leu Glu
        195             200             205

Pro Asp Thr Tyr Cys Arg Tyr Asp Ser Val Ser Val Phe Asn Gly Ala
    210             215             220

Val Ser Asp Asp Ser Arg Arg Leu Gly Lys Phe Cys Gly Asp Ala Val
225             230             235             240

Pro Gly Ser Ile Ser Ser Glu Gly Asn Glu Leu Leu Val Gln Phe Val
            245             250             255

Ser Asp Leu Ser Val Thr Ala Asp Gly Phe Ser Ala Ser Tyr Lys Thr
            260             265             270

Leu Pro Arg Gly Thr Ala Lys Glu Gly Gln Gly Pro Gly Pro Lys Arg
            275             280             285

Gly Thr Glu Pro Lys Val Lys Leu Pro Pro Lys Ser Gln Pro Pro Glu
            290             295             300

Lys Thr Glu Glu Ser Pro Ser Ala Pro Asp Ala Pro Thr Cys Pro Lys
305             310             315             320

Gln Cys Arg Arg Thr Gly Thr Leu Gln Ser Asn Phe Cys Ala Ser Ser
            325             330             335

Leu Val Val Thr Ala Thr Val Lys Ser Met Val Arg Glu Pro Gly Glu
            340             345             350

Gly Leu Ala Val Thr Val Ser Leu Ile Gly Ala Tyr Lys Thr Gly Gly
            355             360             365

Leu Asp Leu Pro Thr Pro Pro Thr Gly Ala Ser Leu Lys Phe Tyr Val
    370             375             380

Pro Cys Lys Gln Cys Pro Pro Met Lys Lys Gly Val Ser Tyr Leu Leu
385             390             395             400

Met Gly Gln Val Glu Glu Asn Arg Gly Pro Val Leu Pro Pro Glu Ser
            405             410             415

Phe Val Val Leu His Arg Pro Asn Gln Asp Gln Ile Leu Thr Asn Leu
            420             425             430

Ser Lys Arg Lys Cys Pro Ser Gln Pro Val Arg Ala Ala Ala Ser Gln
        435             440             445

Asp
```